(12) United States Patent
Van Abeelen

(10) Patent No.: US 10,603,509 B2
(45) Date of Patent: Mar. 31, 2020

(54) PHOTOTHERAPY BLANKET TEMPERATURE DETERMINATION

(71) Applicant: KONINKLIJKE PHILIPS N.V., Eindhoven (NL)

(72) Inventor: Frank Anton Van Abeelen, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 508 days.

(21) Appl. No.: 15/326,517

(22) PCT Filed: Jul. 27, 2015

(86) PCT No.: PCT/IB2015/055670
§ 371 (c)(1),
(2) Date: Jan. 16, 2017

(87) PCT Pub. No.: WO2016/016792
PCT Pub. Date: Feb. 4, 2016

(65) Prior Publication Data
US 2017/0203122 A1    Jul. 20, 2017

Related U.S. Application Data

(60) Provisional application No. 62/030,354, filed on Jul. 29, 2014.

(51) Int. Cl.
*A61N 5/06*       (2006.01)
*A61B 5/01*       (2006.01)
(Continued)

(52) U.S. Cl.
CPC .............. *A61N 5/0621* (2013.01); *A61B 5/01* (2013.01); *A61N 5/0625* (2013.01);
(Continued)

(58) Field of Classification Search
CPC .................. A61B 5/01; A61B 5/02055; A61B 2018/00648; A61N 5/0625
See application file for complete search history.

(56) References Cited

U.S. PATENT DOCUMENTS 6,290,713 B1    9/2001    Russel
8,756,731 B1    6/2014    Huttner et al.
(Continued)

FOREIGN PATENT DOCUMENTS

| CN | 103845812 A | 6/2014 |
|---|---|---|
| WO | 2014006537 A2 | 1/2014 |
| WO | 2014024092 A1 | 2/2014 |

OTHER PUBLICATIONS

Natus Newborn Care, Neoblue Blanket, LED Phototherapy, Natus Medical Incorporated, Downloaded From www.natus.com 2012, 4 Pages.

*Primary Examiner* — Lynsey C Eiseman
*Assistant Examiner* — Amanda L Steinberg

(57) ABSTRACT

Systems and methods for determining one or more temperatures within a phototherapy blanket use or include one or more temperature sensors and a set of light sources to determine a temperature of a subject undergoing phototherapy within the phototherapy blanket and estimate a core temperature of the subject based on, at least, the temperature. The phototherapy blanket may include a thicker region having a higher thermal insulation than one or more other regions of the phototherapy blanket. By virtue of measuring the temperature at or near the thicker region, the uncertainty in the relation between a temperature and the subject's core temperature may be reduced, for more accurate temperature determination within the phototherapy blanket.

17 Claims, 4 Drawing Sheets

(51) Int. Cl.
*A61B 18/00* (2006.01)
*A61F 7/00* (2006.01)
*A61B 17/00* (2006.01)

(52) U.S. Cl.
CPC ............... *A61B 2017/00084* (2013.01); *A61B 2018/00648* (2013.01); *A61B 2018/00678* (2013.01); *A61B 2018/00702* (2013.01); *A61B 2018/00797* (2013.01); *A61B 2503/04* (2013.01); *A61F 7/0097* (2013.01); *A61F 2007/0096* (2013.01); *A61N 2005/0626* (2013.01); *A61N 2005/0627* (2013.01); *A61N 2005/0636* (2013.01); *A61N 2005/0637* (2013.01); *A61N 2005/0645* (2013.01); *A61N 2005/0652* (2013.01); *A61N 2005/0653* (2013.01); *A61N 2005/0663* (2013.01)

(56) References Cited

U.S. PATENT DOCUMENTS

| | | | |
|---|---|---|---|
| 2003/0040783 A1* | 2/2003 | Salmon | A61F 7/02 607/111 |
| 2004/0064170 A1 | 4/2004 | Radons et al. | |
| 2010/0094385 A1 | 4/2010 | Hendriks et al. | |
| 2010/0179469 A1 | 7/2010 | Hammond et al. | |
| 2011/0190594 A1 | 8/2011 | Heit et al. | |
| 2012/0330388 A1 | 12/2012 | Chen et al. | |
| 2013/0274840 A1* | 10/2013 | McLeod | A61F 7/00 607/100 |
| 2014/0275742 A1 | 9/2014 | Andrew | |

* cited by examiner

PHOTOTHERAPY BLANKET TEMPERATURE DETERMINATION

CROSS-REFERENCE TO PRIOR APPLICATIONS

This application is the U.S. National Phase application under 35 U.S.C. § 371 of International Application No. PCT/IB2015/055670, filed on Jul. 27, 2015, which claims the benefit of U.S. Provisional Patent Application No. 62/030,354, filed on Jul. 29, 2014. These applications are hereby incorporated by reference herein.

BACKGROUND

1. Field

The present disclosure pertains to systems and methods for determining one or more temperatures within a phototherapy blanket, and, in particular, to systems and methods to estimate a core temperature of a subject undergoing phototherapy treatment.

2. Description of the Related Art

Infants, e.g. neonates, may be treated with phototherapy. An example of phototherapy is jaundice treatment using light sources that emit, e.g., blue light. The core temperature of infants commonly needs to be monitored and/or determined accurately. Light sources commonly emit heat in addition to light, or otherwise add or provide heat and/or energy to their environment. Light and/or other electromagnetic radiation provided to and/or emitted in proximity of an infant may contribute to the thermal environment and/or core temperature of the infant.

SUMMARY

Accordingly, it is an object of one or more embodiments of the present invention to provide a system for determining one or more temperatures inside a phototherapy blanket. The system comprises a blanket used to provide phototherapy, a set of light sources, a temperature sensor, and one or more physical computer processors. The blanket may be referred to as a photo-therapy blanket. The phototherapy blanket is configured to cover, support, and/or envelop at least part of a subject. The phototherapy blanket includes a first region having a first level of thermal insulation and a second region having a second level of thermal insulation. The first level is greater than the second level. The set of light sources is configured to emit electromagnetic radiation. The set of light sources is held and/or carried by the phototherapy blanket. The temperature sensor generates one or more output signals conveying information related to a first temperature in or near the phototherapy blanket. The one or more physical computer processors are operatively coupled with the temperature sensor. The one or more physical computer processors are configured to determine the first temperature based on the one or more output signals, obtain an amount of power dissipated in one or more light sources from the set of light sources, estimate a core temperature of the subject based on (a) the first temperature, and (b) the obtained amount of power, and control the set of light sources based on the estimated core temperature.

It is yet another aspect of one or more embodiments of the present invention to provide a method for determining a temperature inside a phototherapy blanket. The phototherapy blanket includes a first region having a first level of thermal insulation and a second region having a second level of thermal insulation. The first level is greater than the second level. The method comprises holding and/or carrying a set of light sources; emitting electromagnetic radiation inside the phototherapy blanket; generating a first output signal conveying information related to a first temperature in or near the phototherapy blanket; determining the first temperature based on the first output signal; obtaining an amount of power dissipated in one or more light sources from the set of light sources; estimating a core temperature of the subject based on (a) the first temperature, and (b) the obtained amount of power; and controlling the set of light sources based on the estimated core temperature.

It is yet another aspect of one or more embodiments to provide a system configured to determine a temperature inside a phototherapy means. The phototherapy means includes a first region having a first level of thermal insulation and a second region having a second level of thermal insulation. The first level is greater than the second level. The system comprises means for holding and/or carrying means for emitting electromagnetic radiation; the means for emitting electromagnetic radiation inside the phototherapy blanket, wherein the electromagnetic radiation is configured to provide phototherapy; means for generating a first output signal conveying information related to a first temperature in or near the phototherapy means; means for determining the first temperature based on the first output signal; means for obtaining an amount of power dissipated in the means for emitting electromagnetic radiation; means for estimating a core temperature of the subject based on (a) the first temperature, and (b) the obtained amount of power; and means for controlling the means for emitting electromagnetic radiation based on the estimated core temperature.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

DETAILED DESCRIPTION OF EXEMPLARY EMBODIMENTS

Figure 1:
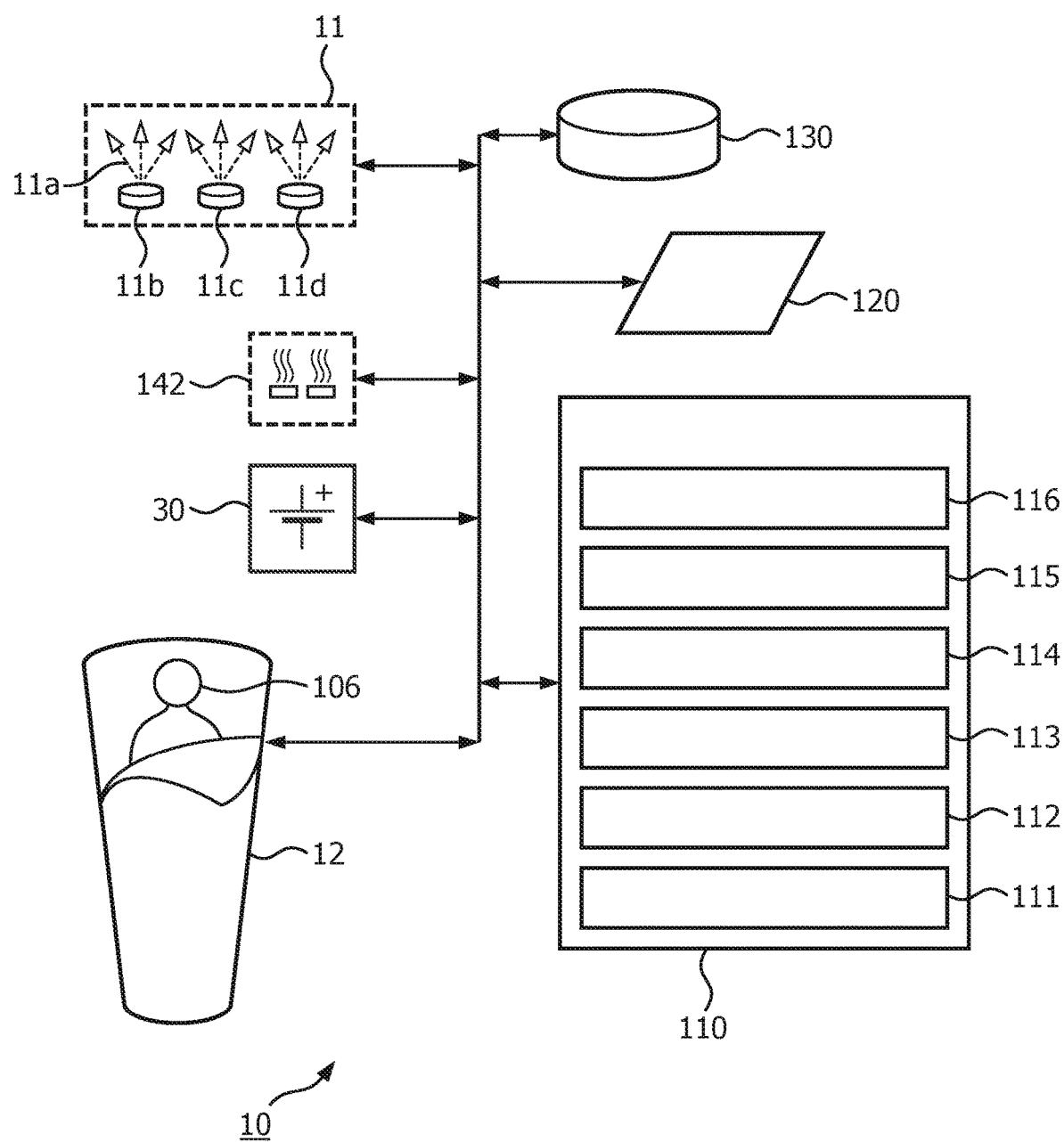
FIG. 1 schematically illustrates a system in accordance with one or more embodiments.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled"

means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

As used herein, the term "obtain" (and derivatives thereof) may include active and/or passive retrieval, programming, determination, derivation, transfer, and/or exchange of information, and/or any combination thereof.

For illustrative purposes, the treatment of a newborn baby or neonate at home, in a baby ward, or in a Neonatal Intensive Care Unit (NICU) is used as an exemplary embodiment. Note that the scope of this disclosure is not limited to a specific class or type of patients, such as neonates. Instead, treatment of adults and other subjects is contemplated within the scope of this disclosure. FIG. 1 schematically illustrates a system 10 including a phototherapy blanket 12, a set of light sources 11 (which may in some implementations include a driver), one or more temperature sensors 142, one or more processors 110, a power supply 30 (which may in some implementations include a driver), a user interface 120, electronic storage 130, one or more computer program components, and/or other components, in accordance with one or more embodiments. System 10 is configured to determine and/or control one or more temperatures inside phototherapy blanket 12 and/or one or more temperatures on and/or near a subject 106. Note that system 10 is not restricted or limited to be used in or with incubators, heat lamps, or infant warmers, though a NICU environment may be a suitable for determining and/or controlling temperatures for subjects. System 10 may be integrated, embedded, incorporated, combined, and/or otherwise operating in conjunction with an incubator, baby warmer, a subject monitoring device (a.k.a. a patient monitor), a respiratory device, a respiratory monitor, and/or medical apparatus used for treatment of infants.

Figure 2:
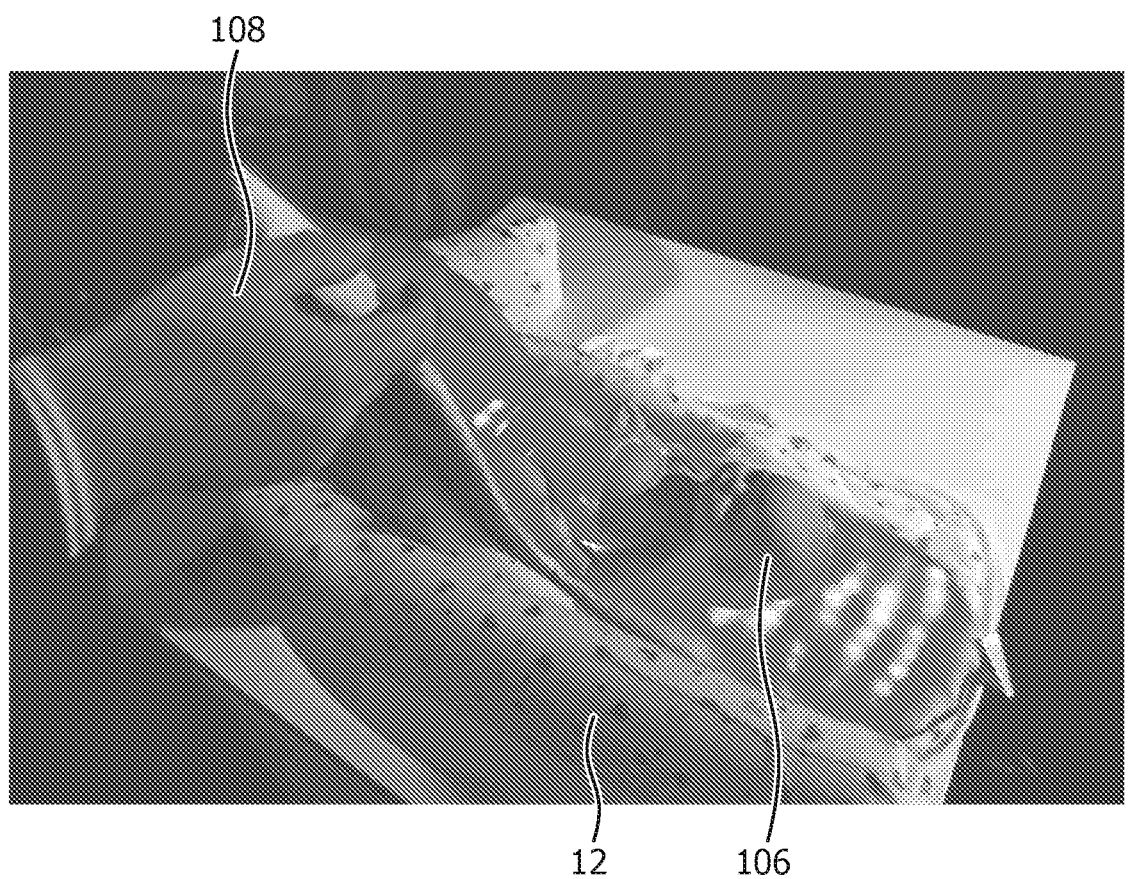
FIG. 2 illustrates an exemplary embodiment for determining temperatures inside a phototherapy blanket.

Phototherapy blanket 12 may be configured to cover, support, and/or envelop at least part of subject 106. Phototherapy blanket 12 may include structure to support subject 106. By way of non-limiting example, phototherapy blanket 12 may include one or more of a mattress, a pad, a blanket, a sleeping bag, textile layers, and/or other suitable structures to cover, support, and/or envelop at least part of subject 106. For example, as illustrated in FIG. 2, phototherapy blanket 12 may be implemented in a shape similar to a sleeping bag.

In some implementations, different regions, sections, areas, and/or portions of phototherapy blanket 12 may include different materials and/or have different thermal characteristics. For example, a first region of phototherapy blanket 12 may have a first level of thermal insulation; a second region of phototherapy blanket 12 may have a second level of thermal insulation, and so forth. In some implementations, the first level of insulation may be greater than the second level of insulation. For example, in some implementations, at least part of the bottom of phototherapy blanket 12 on which subject 106 is supported may have a higher level of thermal insulation than at least part of the remainder of phototherapy blanket 12. In some implementations, the first region may be disposed opposite the second region. For example, for subject 106 in a supine position, the first region may be closer to the back of subject 106 than the second region, and the second region may be closer to the front of subject 106 than the first region. In some implementations, it may be preferred, e.g. for heat management and/or to allow more phototherapy treatment, to limit the size of the region having a higher level of thermal insulation. In some implementations, it may be preferred that the region having a higher level of thermal insulation is on the bottom during use and/or treatment.

Figure 3A:
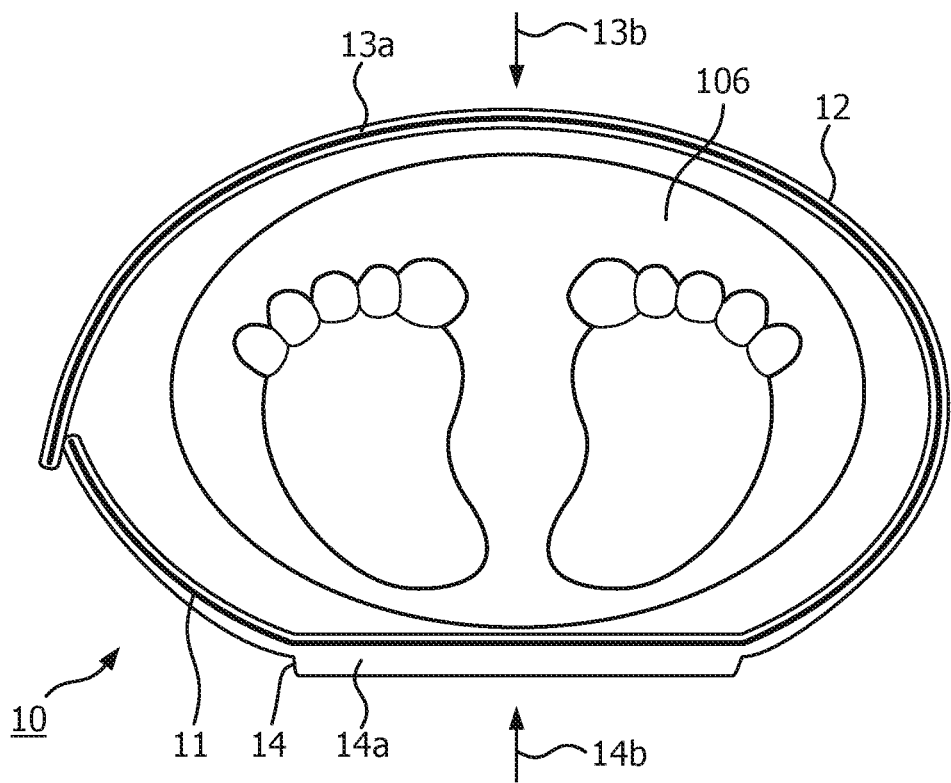
FIGS. 3A and 3B schematically illustrate exemplary embodiments for determining temperatures inside a phototherapy blanket.

By way of non-limiting example, FIG. 3A illustrates a phototherapy blanket 12 including a first region 14a on a first side 14b having a first level of thermal insulation, by virtue of structural component 14 (e.g. a particular material, layer, or variation of thickness thereof). Phototherapy blanket 12 further includes a second region 13a on a second side 13b having a second level of thermal insulation. The first level of insulation may be greater than the second level of insulation. For example, a greater portion of the heat provided through set of light sources 11 (indicated in FIG. 3A as a thick line embedded within phototherapy blanket 12 and enveloping subject 106) in first region 14a may contribute to a core temperature, skin temperature, and/or another temperature of subject 106 in or near region 14a, compared, e.g. per unit area, to a relatively smaller portion of the heat provided through set of light sources 11 in second region 13a (contributing to a core temperature, skin temperature, and/or another temperature of subject 106 in or near region 13a). In some implementations, the transfer and/or dissipation of heat and/or energy from subject 106 to the environment may be more efficient through second region 13a than through first region 14a.

In some implementations, a particular region, section, area, and/or portion of phototherapy blanket 12 may include a material, component, and/or layer having a known heat transfer coefficient (e.g. thermal conductance per unit area). By way of non-limiting example, such a material, component, and/or layer is labeled 15 in FIG. 3B (jointly referred to as component 15).

Referring to FIG. 1, set of light sources 11 may be included in system 10, for example held and/or carried by phototherapy blanket 12. Set of light sources 11 may be configured to emit electromagnetic radiation 11a. Set of light sources 11 may include multiple light sources, for example a first light source 11b, a second light source 11c, a third light source 11d, and so forth. The illustration of set of light sources 11 including three members in FIG. 1 is not intended to be limiting. System 10 may include one or more light sources.

In some implementations, set of light sources 11 may include one or more light-emitting diodes (LEDs). In some implementations, set of light sources 11 may include one or more organic light-emitting diodes (OLEDs). Emitted electromagnetic radiation 11a may be configured to provide therapy (e.g. phototherapy) to subject 106. For example, in some implementations, electromagnetic radiation 11a may be used to treat jaundice and/or hyper-bilirubinemia in an infant. For example, blue light having particular electromagnetic characteristics may be used to provide treatment and/or therapy.

Power supply 30 may be configured to provide the power to operate and/or activate one or more light sources from set of light sources 11. In some implementations, power supply 30 may be configured to operate a driver to activate one or more light sources from set of light sources 11. Set of light sources 11 may be configured, through emitted electromagnetic radiation 11a and/or power dissipated within set of light sources 11, to provide treatment to subject 106, e.g. through heat, energy, and/or power. Heat, energy, and/or power provided to subject 106 through system 10 and/or phototherapy blanket 12 (whether intentional or not) may contribute to one or more current temperatures of subject 106, including but not limited to the core temperature of subject 106. One or more temperatures of subject 106 may need to be monitored and/or controlled accurately.

Figure 3B:
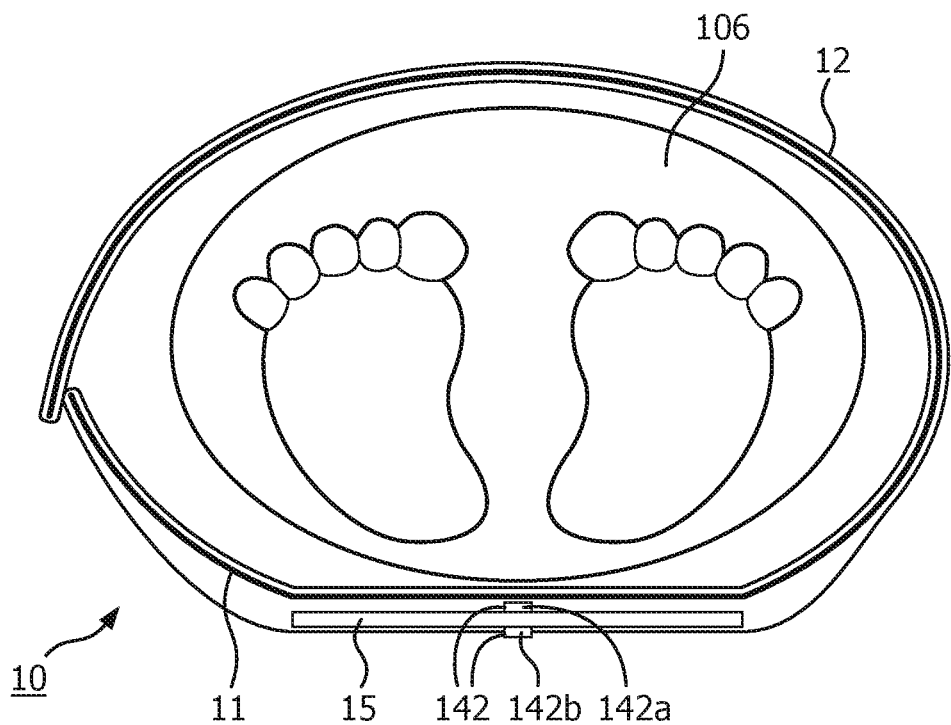

One or more temperature sensors 142 of system 10 may be configured to generate output signals conveying information related to one or more temperatures. The temperatures may include one or more temperatures in or near phototherapy blanket 12, one or more temperatures of subject 106, and/or other temperatures. For example, a temperature sensor 142 may be configured to generate output signals conveying information regarding a skin temperature of subject 106. For example, a temperature sensor or infrared (IR) sensor in proximity of the skin may be configured to generate output signals conveying information regarding the skin temperature. The illustration of temperature sensor 142 including two members in FIG. 1 or FIG. 3B are not intended to be limiting. System 10 may include one or more temperature sensors 142. In some implementations, system 10 may include three or more temperature sensors 143, e.g. to reduce variations in measurements.

In some implementations, system 10 may include other sensors (not shown in FIG. 1) that may be configured to generate output signals conveying (current) physiological information and/or measurements for subject 106. In some embodiments, the generated output signals may convey one or more of the status of system 10, medical parameters related to subject 106, environmental parameters, respiratory treatment-specific parameters, and/or subject-specific parameters. For example, the other sensors may include one or more of a heart rate sensor, a respiratory rate sensor, an oxygen sensor, a bilirubin sensor, a tidal volume sensor, an airflow sensor, a pressure sensor, a weight sensor, a still-image camera, a video camera, a microphone, and/or other sensors.

Resulting signals or information from temperature sensors 142 and/or other sensors may be transmitted to processor 110, user interface 120, electronic storage 130, and/or other components of system 10. This transmission can be wired and/or wireless.

User interface 120 of system 10 in FIG. 1 may be configured to provide an interface between system 10 and a user (e.g., user 108 as illustrated in FIG. 2, a caregiver, a healthcare provider, a therapy decision-maker, a medical professional etc.) through which the user can provide information to and receive information from system 10. This enables data, results, and/or instructions and any other communicable items, collectively referred to as "information," to be communicated between the user and system 10. An example of information that may be conveyed to a user is a report detailing the changes in monitored temperature throughout a period during which subject 106 is present. Examples of interface devices suitable for inclusion in user interface 120 include a keypad, buttons, switches, a keyboard, knobs, levers, a display screen, a touch screen, speakers, a microphone, an indicator light, an audible alarm, and a printer. Information may be provided to a user by user interface 120 in the form of auditory signals, visual signals, tactile signals, and/or other sensory signals, or any combination thereof.

By way of non-limiting example, user interface 120 may include a radiation source capable of emitting light. The radiation source may include, for example, one or more of at least one LED, at least one light bulb, a display screen, and/or other sources. User interface 120 may control the radiation source to emit light in a manner that conveys to a user information related to a temperature of subject 106 and/or other information.

It is to be understood that other communication techniques, either hard-wired or wireless, are contemplated herein as user interface 120. For example, in one embodiment, user interface 120 may be integrated with a removable storage interface provided by electronic storage 130. In this example, information is loaded into system 10 from removable storage (e.g., a smart card, a flash drive, a removable disk, etc.) that enables the user(s) to customize the implementation of system 10. Other exemplary input devices and techniques adapted for use with system 10 as user interface 120 include, but are not limited to, an RS-232 port, RF link, an IR link, a USB connection, modem (telephone, cable, Ethernet, internet or other). In short, any technique for communicating information with system 10 is contemplated as user interface 120.

Electronic storage 130 of system 10 in FIG. 1 includes electronic storage media that electronically stores information. The electronic storage media of electronic storage 130 may include one or both of system storage that is provided integrally (i.e., substantially non-removable) with system 10 and/or removable storage that is removably connectable to system 10 via, for example, a port (e.g., a USB port, a FireWire port, etc.) or a drive (e.g., a disk drive, etc.). Electronic storage 130 may include one or more of optically readable storage media (e.g., optical disks, etc.), magnetically readable storage media (e.g., magnetic tape, magnetic hard drive, floppy drive, etc.), electrical charge-based storage media (e.g., EPROM, EEPROM, RAM, etc.), solid-state storage media (e.g., flash drive, etc.), and/or other electronically readable storage media. Electronic storage 130 may store software algorithms, information determined by processor 110, information received via user interface 120, and/or other information that enables system 10 to function properly. For example, electronic storage 130 may record or store one or more measured temperatures, and/or other information. Electronic storage 130 may be a separate component within system 10, or electronic storage 130 may be provided integrally with one or more other components of system 10 (e.g., processor 110).

Processor 110 of system 10 in FIG. 1 is configured to provide information processing capabilities in system 10. As such, processor 110 includes one or more of a digital processor, an analog processor, a digital circuit designed to process information, an analog circuit designed to process information, and/or other mechanisms for electronically processing information. Although processor 110 is shown in FIG. 1 as a single entity, this is for illustrative purposes only. In some implementations, processor 110 includes a plurality of processing units.

As is shown in FIG. 1, processor 110 is configured to execute one or more computer program components. The one or more computer program components include one or more of temperature determination component 111, power dissipation component 112, estimation component 113, control component 114, treatment component 115, parameter determination component 116, and/or other components. Processor 110 may be configured to execute components 111, 112, 113, 114, 115, and/or 116 by software; hardware; firmware; some combination of software, hardware, and/or firmware; and/or other mechanisms for configuring processing capabilities on processor 110.

It should be appreciated that although components 111-116 are illustrated in FIG. 1 as being co-located within a single processing unit, in implementations in which processor 110 includes multiple processing units, one or more of components 111-116 may be located remotely from the other components. The description of the functionality provided by the different components 111-116 described below is for illustrative purposes, and is not intended to be limiting, as any of components 111-116 may provide more or less functionality than is described. For example, one or more of components 111-116 may be eliminated, and some or all of its functionality may be provided by other ones of components 111-116. Note that processor 110 may be configured to execute one or more additional components that may perform some or all of the functionality attributed below to one of components 111-116.

Subject 106 may be monitored during operation of system 10 or a component thereof, e.g. while undergoing treatment. In some embodiments, subject 106 may be monitored using one or more temperature sensors 142. For example, temperature sensor 142 may be configured to generate output signals conveying physiological information for subject 106, including but not limited to a skin temperature and/or a temperature at a location in proximity of subject 106.

Temperature determination component 111 may be configured to determine one or more temperatures in or near phototherapy blanket 12, one or more temperatures of subject 106, and/or other temperatures. Determinations by temperature determination component 111 may be based on output signals from sensors, including but not limited to one or more temperature sensors 142. In some implementations, temperature determination component 111 may be configured to determine a skin temperature of subject 106, e.g. within phototherapy blanket 12. Skin temperature may be referred to as $T_s$. In some implementations, temperature determination component 111 may be configured to determine one or more temperatures within phototherapy blanket, on or near a particular region, section, area, and/or portion of phototherapy blanket 12, and/or on or near one or both sides of a particular material, component, and/or layer included in phototherapy blanket 12.

For example, referring to FIG. 3B, temperature determination component 111 may be configured to determine a first temperature (referred to as $T_{in}$) on the inward-facing side of component 15, a second temperature (referred to as $T_{out}$) on the outward-facing side of component 15, and/or other temperatures. As used herein, the term "inward-facing" may be used to indicate the side or direction facing towards subject 106 during usage of system 10, and "outward-facing" may be used to indicate the side or direction facing away from subject 106 during usage of system 10. As illustrated in FIG. 3B, system 10 may include multiple temperature sensors 142, for example a first temperature sensor 142a and a second temperature sensor 142b. For example, the first temperature may be based on output signals generated by first temperature sensor 142a, and the second temperature may be based on output signals generated by second temperature sensor 142b. First temperature sensor 142a may be disposed on the inward-facing side of component 15, and second temperature sensor 142b may be disposed on the outward-facing side of component 15. In some implementations, component 15 may have known thermal characteristics, including but not limited to a known heat transfer coefficient K (i.e. thermal conductance per unit area).

Power dissipation component 112 may be configured to obtain and/or determine an amount of power dissipated in one or more light sources from set of light sources 11. In some implementations, power dissipation component 112 may be configured to obtain and/or determine a heat flux introduced by one or more light sources from set of light sources 11. In some implementations, power dissipation component 112 may be configured to obtain information through programming, including but not limited to programming that is performed prior to treatment of a user. As used herein, the term "determine" (and derivatives thereof) may include measure, calculate, compute, estimate, approximate, generate, and/or otherwise derive, and/or any combination thereof.

In some implementations, the amount of power dissipated, as obtained and/or determined by power dissipation component 112, may be related to a subset of the set of light sources 11, for example one or more light sources in proximity to a particular temperature sensor 142, and/or the one or more light sources that affect, to a sufficiently substantial degree, the relationship between the core temperature and a particular skin temperature $T_s$. In some implementations, such a degree may be based on a particular percentage of the measured/determined temperature that is equivalent to a particular percentage of the measured/determined temperature. Particular percentages may be 2%, 1%, 0.5%, 0.1%, and/or another percentage. In some implementations, the amount of power dissipated may be based on, related to, or equal to the electrical power dissipated by one or more light sources from set of light sources 11. The amount of power or heat flux as obtained and/or determined by power dissipation component 112, expressed per unit area (as average heat flux density), may be referred to as "p".

Estimation component 113 may be configured to estimate and/or determine a core temperature of subject 106. Core temperature may be referred to as $T_c$. Estimations and/or determinations by estimation component 113 may be based on one or more temperatures, e.g. as determined by temperature determination component 111. Alternatively, and/or simultaneously, estimations and/or determinations by estimation component 113 may be based on an obtained and/or determined amount of power and/or heat flux, e.g. as obtained and/or determined by power dissipation component 112. For example, in some implementations, estimations and/or determinations by estimation component 113 may be based on the following formula:

$$p-q=K_s(T_s-T_c), \quad [1]$$

wherein $T_s$ is the skin temperature of subject 106, $T_c$ is the core temperature of subject 106, p is the amount of power or heat flux per unit area as obtained and/or determined by power dissipation component 112, $K_s$ may be a heat transfer coefficient for the skin of subject 106, and q is the thermal flux density towards the environment for the particular region, section, area, and/or portion of phototherapy blanket 12 where the measurement of $T_s$ is taken. In some implementations, $K_s$ may be obtained and/or measured by system 10, e.g. by estimation component 113. In some implementations, $K_s$ may be estimated based on average and/or typical skin characteristics known in the pertinent fields of technology related to skin temperatures.

In some implementations, using measurements of $T_s$ taken at or near a particular region, section, area, and/or portion of phototherapy blanket 12 where the level of thermal insulation is sufficiently high (e.g. first region 14a as depicted in FIG. 3A), thermal heat flux density q may be assumed and/or approximated as zero. For example, thermal heat flux density q may be assumed and/or approximated as zero if the level of thermal insulation is so high that the relationship between $T_s$ and $T_c$ is substantially unaffected by environmental conditions around phototherapy blanket 12 and/or subject 106, including but not limited to whether subject 106 is being held, e.g. for kangaroo care, or not, how phototherapy blanket 12 and/or subject 106 are positioned, which materials are used to cover subject 106, the room temperature, and/or other changes that may affect thermal conditions of subject 106 during treatment. In some implementations, the term "substantially unaffected" may be based on a particular percentage of a measured and/or determined temperature. Particular percentages may be 2%, 1%, 0.5%, 0.1%, and/or another percentage. In some implementations, the term "substantially unaffected" may be based on the absolute effect on the measured relationship, e.g. 0.1 K, 0.2 K, 0.3 K, 0.4 K, 0.5 K, 0.6 K, 0.7 K, 0.8 K, 0.9 K, 1 K, and/or another absolute temperature differential. The preceding formula [1] may reduce to the following formula:

$$T_c = (T_s - p/K_s) \quad [2]$$

Referring to FIG. 3B, in some implementations, multiple temperature sensors 142 may be used to determine temperatures $T_{in}$ and $T_{out}$ on opposite sides of structural component 15, having known heat transfer coefficient K. Note that thermal heat flux density q may vary dynamically, over time, and/or based on whether subject 106, while within phototherapy blanket 12, is being held or not. For example, q may vary as the position of phototherapy blanket 12 and/or subject 106 changes, as the materials used to cover subject 106 change, as environmental conditions change, including but not limited to ambient temperature and/or humidity, as the air flow around phototherapy blanket 12 and/or subject 106 changes, and/or based on changes in the status or condition of subject 106. Thermal heat flux density q may be determined based on the following formula:

$$q = K(T_{in} - T_{out}) \quad [3]$$

In some implementations, determinations of thermal heat flux density q may be made dynamically, repeatedly, continuously, continually, and/or in other suitable ways to monitor q and/or $T_c$. In some implementations, $T_{in}$ and $T_s$ may be based on output signals generated by the same temperature sensor 142. In some implementations, $T_{in}$ and $T_s$ may be based on output signals generated by different temperature sensors 142. In some implementations, determinations of thermal heat flux density q may be made by parameter determination component 116. For example, parameter determination component 116 may be configured to determine a particular heat flux density in a particular region, section, area, and/or portion of phototherapy blanket 12 (e.g. in proximity of component 15 as depicted in FIG. 3B) based on one or more temperatures (e.g. as determined by temperature determination component 111, including but not limited to $T_s$, $T_{in}$, and/or $T_{out}$).

Control component 114 may be configured to control set of light sources 11 and/or thereby affect one or more temperatures within system 10, including but not limited to the core temperature of subject 106. For example, control may be based on one or more estimations and/or determinations by estimation component 113. In some implementations, control component 114 may obtain and/or determine a threshold core temperature for subject 106, and adjust set of light sources 11 accordingly based on whether the determined and/or estimated core temperature of subject 106 breaches the threshold core temperature. In some implementations, control component 114 may be configured to adjust and/or control the amount of power supplied to set of light sources 11 based on a difference between the threshold core temperature and the current determined and/or estimated core temperature of subject 106. For example, responsive to the determined and/or estimated core temperature of subject 106 being higher than the threshold core temperature, control component 114 may be configured to reduce, possibly to zero, the amount of power supplied to one or more light sources in set of light sources 11. For example, responsive to the determined and/or estimated core temperature of subject 106 being lower than the threshold core temperature, control component 114 may increase the amount of power supplied to one or more light sources in set of light sources 11. In some implementations, controlling the amount of power being supplied to one or more light sources in set of light sources 11 may be accomplished by adjusting the settings and/or operating parameters of a driver, e.g. included with set of light sources 11 or power supply 30.

Treatment component 115 may be configured to determine and/or obtain one or more threshold temperatures, e.g. a threshold core temperature for subject 106. In some implementations, a threshold core temperature may be obtained through medical professionals and/or programmed based on standard guidelines for infants.

Figure 4:
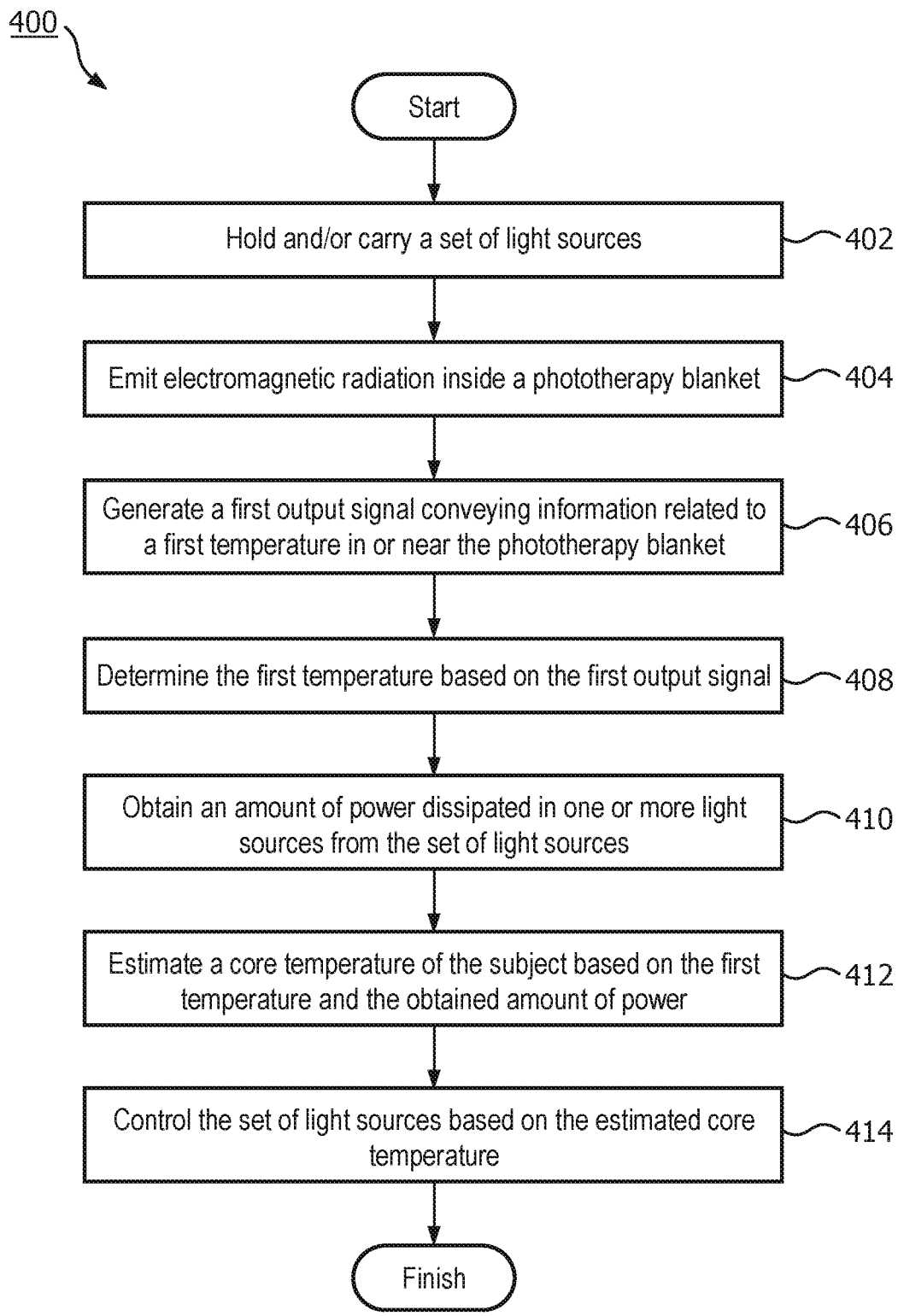
FIG. 4 illustrates a method for determining temperatures inside a phototherapy blanket in accordance with one or more embodiments.

FIG. 4 illustrates a method 400 for determining temperatures inside a phototherapy blanket, for example a phototherapy blanket 12 as described in this disclosure. The operations of method 400 presented below are intended to be illustrative. In some embodiments, method 400 may be accomplished with one or more additional operations not described, and/or without one or more of the operations discussed. Additionally, the order in which the operations of method 400 are illustrated in FIG. 4 and described below is not intended to be limiting.

In some embodiments, method 400 may be implemented in (and/or using) one or more processing devices (e.g., a digital processor, an analog processor, a digital circuit designed to process information, an analog circuit designed to process information, and/or other mechanisms for electronically processing information). The one or more processing devices may include one or more devices executing at least some of the operations of method 400 in response to instructions stored electronically on an electronic storage medium. The one or more processing devices may include one or more devices configured through hardware, firmware, and/or software to be specifically designed for execution of one or more of the operations of method 400.

At an operation 402, a set of light sources is held and/or carried. In some embodiments, operation 402 is performed by a phototherapy blanket the same as or similar to phototherapy blanket 12 (shown in FIG. 2 and described herein).

At an operation 404, electromagnetic radiation is emitted inside the phototherapy blanket. In some embodiments, operation 404 is performed by a set of light sources the same as or similar to set of light sources 11 (shown in FIG. 1 and described herein).

At an operation 406, a first output signal is generated that conveys information related to a first temperature in or near the phototherapy blanket. In some embodiments, operation 406 is performed by a temperature sensor the same as or similar to temperature sensor 142 (shown in FIG. 1 and described herein).

At an operation 408, the first temperature is determined based on the first output signal. In some embodiments, operation 408 is performed by a temperature determination component the same as or similar to temperature determination component 111 (shown in FIG. 1 and described herein).

At an operation 410, an amount of power is obtained that is dissipated in one or more light sources from the set of light sources. In some embodiments, operation 410 is performed by a power dissipation component the same as or similar to power dissipation component 112 (shown in FIG. 1 and described herein).

At an operation 412, a core temperature of the subject is estimated based on the first temperature and the obtained amount of power. In some embodiments, operation 412 is performed by an estimation component the same as or similar to estimation component 113 (shown in FIG. 1 and described herein). In some implementations, a notification or alarm may be issued based on the estimated core temperature, e.g. if the core temperature is too high. In some implementations, operation 414 may not be performed.

At an operation 414, the set of light sources is controlled based on the estimated core temperature. In some embodiments, operation 414 is performed by a control component the same as or similar to control component 114 (shown in FIG. 1 and described herein).

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A system for determining temperatures inside a phototherapy blanket, wherein the phototherapy blanket is configured to cover, support, and/or envelop at least part of a subject, the system comprising:
a set of light sources configured to emit electromagnetic radiation and configured to be held and/or carried by the phototherapy blanket;
a first temperature sensor that is configured to generate a first output signal conveying information related to a first temperature in the phototherapy blanket;
one or more physical computer processors operatively coupled with the first temperature sensor, the one or more physical computer processors configured to:
determine the first temperature based on the first output signal;
obtain an amount of power dissipated in one or more light sources from the set of light sources;
estimate a core temperature of the subject based on:
(a) the first temperature, and
(b) the obtained amount of power; and
control the set of light sources based on a comparison of a threshold core temperature to the estimated core temperature.

2. The system of claim 1, wherein the one or more physical computer processors are further configured to obtain the threshold core temperature for the subject, wherein the set of light sources are controlled based on a difference between the estimated core temperature and the threshold core temperature.

3. The phototherapy blanket system of claim 1, wherein the set of light sources includes light-emitting diodes (LEDs) and the first temperature sensor is held and/or carried in the first region.

4. The phototherapy blanket system of claim 3, wherein the first region includes a component having an inward-facing side and an outward-facing side, the first temperature sensor is disposed at or near the inward-facing side, and the system for determining temperatures further comprises:
a second temperature sensor configured to generate a second output signal conveying information related to a second temperature in the phototherapy blanket, wherein the second temperature sensor is disposed in or near the outward-facing side, and the one or more physical processors are further configured to:
determine the second temperature based on the second output signal;
determine a heat flux density through the first region based on the first temperature and the second temperature, wherein estimation of the core temperature is further based on the heat flux density.

5. The phototherapy blanket system of claim 4, further comprising:
a third temperature sensor configured to generate a third output signal conveying information related to a temperature in or near the phototherapy blanket, wherein the third temperature sensor is disposed to convey the information related to the temperature in or near the phototherapy blanket and estimation of the core temperature is further based on the temperature in or near the phototherapy blanket.

6. A method for determining a temperature inside a phototherapy blanket, wherein the phototherapy blanket includes a first region having a first level of thermal insulation and a second region having a second level of thermal insulation and the first level is greater than the second level, the method comprising:
holding and/or carrying a set of light sources for emitting electromagnetic radiation inside the phototherapy blanket;
generating a first output signal conveying information related to a first temperature in the phototherapy blanket;
determining the first temperature based on the first output signal;
obtaining an amount of power dissipated in one or more light sources from the set of light sources;
estimating a core temperature of the subject based on:
(a) the first temperature, and
(b) the obtained amount of power; and
controlling the set of light sources based on a comparison of a threshold core temperature to the estimated core temperature.

7. The method of claim 6, further comprising:
obtaining the threshold core temperature for the subject, wherein the step of controlling the set of light sources is performed based on a difference between the estimated core temperature and the threshold core temperature.

8. The method of claim 6, wherein determining the first temperature is performed by a first temperature sensor that is held and/or carried in the first region.

9. The method of claim 8, wherein the first region includes a component having an inward-facing side and an outward-facing side, the first temperature sensor is disposed at or near the inward-facing side, and the method further comprises:
generating a second output signal conveying information related to a second temperature in the phototherapy blanket, wherein the second temperature sensor is disposed in or near the outward-facing side;
determining the second temperature based on the second output signal; and
determining a heat flux density through the first region based on the first temperature and the second temperature, wherein estimating the core temperature is further based on the heat flux density.

10. The method of claim 9, the method further comprising:
generating a third output signal conveying information related to a temperature in or near the phototherapy blanket, wherein the third temperature sensor is disposed in or near the inward-facing side and estimating the core temperature is further based on the temperature in or near the phototherapy blanket.

11. A system configured to determine a temperature inside a phototherapy means, the system comprising:
means for holding and/or carrying means for emitting electromagnetic radiation inside the phototherapy blanket, wherein the electromagnetic radiation is configured to provide phototherapy;
means for generating a first output signal conveying information related to a first temperature in the phototherapy means;
means for determining the first temperature based on the first output signal;
means for obtaining an amount of power dissipated in the means for emitting electromagnetic radiation;
means for estimating a core temperature of the subject based on:
(a) the first temperature, and
(b) the obtained amount of power; and
means for controlling the means for emitting electromagnetic radiation based on a comparison of a threshold core temperature to the estimated core temperature.

12. The system of claim 11, further comprising:
means for obtaining the threshold core temperature for the subject, wherein operation of the means for controlling is based on a difference between the estimated core temperature and the threshold core temperature.

13. The system of claim 11, wherein the means for determining the first temperature is held and/or carried in the first region.

14. The system of claim 13, wherein the first region includes a component having an inward-facing side and an outward-facing side, the means for determining the first temperature is disposed at or near the inward-facing side, and the system configured to determine a temperature further comprises:
means for generating a second output signal conveying information related to a second temperature in the phototherapy means, wherein the second temperature sensor is disposed in or near the outward-facing side;
means for determining the second temperature based on the second output signal; and
means for determining a heat flux density through the first region based on the first temperature and the second temperature wherein operation of the means for estimating the core temperature is further based on the heat flux density.

15. The system of claim 11, further comprising:
means for generating a third output signal conveying information related to a temperature in or near the phototherapy means, wherein the third temperature sensor is disposed in or near the inward-facing side and operation of the means for estimating the core temperature is further based on the temperature in or near the phototherapy means.

16. A phototherapy blanket system, comprising:
a phototherapy blanket which includes a first region having a first level of thermal insulation and a second region having a second level of thermal insulation, wherein the first level is greater than the second level; and
a system as claimed in claim 1 for determining temperatures inside the phototherapy blanket.

17. A phototherapy system, comprising:
a phototherapy means which includes a first region having a first level of thermal insulation and a second region having a second level of thermal insulation, wherein the first level is greater than the second level; and
a system as claimed in claim 12 for determining temperatures inside the phototherapy means.

* * * * *